(12) United States Patent
Schuppan et al.

(10) Patent No.: US 10,884,001 B2
(45) Date of Patent: Jan. 5, 2021

(54) DIAGNOSIS OF CHRONIC LIVER DISEASES

(71) Applicant: Beth Israel Deaconess Medical Center, Inc., Boston, MA (US)

(72) Inventors: Detlef Schuppan, Mainz (DE); Towia Libermann, Chestnut Hill, MA (US); Simon T. Dillon, Danvers, MA (US); Yury Papou, Boston, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 171 days.

(21) Appl. No.: 15/110,288

(22) PCT Filed: Jan. 9, 2015

(86) PCT No.: PCT/US2015/010859
§ 371 (c)(1),
(2) Date: Jul. 7, 2016

(87) PCT Pub. No.: WO2015/106129
PCT Pub. Date: Jul. 16, 2015

(65) Prior Publication Data
US 2016/0327570 A1    Nov. 10, 2016

Related U.S. Application Data

(60) Provisional application No. 61/926,096, filed on Jan. 10, 2014.

(51) Int. Cl.
*G01N 33/68* (2006.01)
*C07K 14/435* (2006.01)
*C12Q 1/6883* (2018.01)

(52) U.S. Cl.
CPC ....... *G01N 33/6893* (2013.01); *C12Q 1/6883* (2013.01); *C07K 14/435* (2013.01); *C12Q 2600/158* (2013.01); *G01N 2800/085* (2013.01)

(58) Field of Classification Search
None
See application file for complete search history.

(56) References Cited

U.S. PATENT DOCUMENTS

| | | | |
|---|---|---|---|
| 2007/0111933 A1 | 5/2007 | Kopchick et al. | |
| 2011/0129859 A1 | 6/2011 | Tsubouchi et al. | |
| 2013/0034551 A2 | 2/2013 | Satyal et al. | |
| 2013/0183737 A1* | 7/2013 | Borlak | G01N 33/57438 435/190 |

OTHER PUBLICATIONS

Koukoulis et al. Hum Pathol. 2001. 32(12):1356-62.*
Waiker et al (J Am Soc Nephrol. Jan. 2012; 23(1): 13-21) (Year: 2012).*
Mayeux (NeuroRx. Apr. 2004;1(2):182-8) (Year: 2004).*
Morling et al (Clinical Liver Disease, vol. 7, No. 6, Jun. 2016) (Year: 2016).*
Fohey ("Challenges in the Diagnosis of NAFLD, NASH and Comorbidities in the Pediatric Population" published Jan. 24, 2018, downloaded from https://blog.covance.com/2018/01/challenges-in-the-diagnosis-of-nafld-nash-and-comorbidities-in-the-pediatric-population.html) (Year: 2018).*
International Search Report and Written Opinion for International Patent Application No. PCT/US2015/10859, dated Apr. 10, 2015 (17 pages).
International Preliminary Report on Patentability for International Patent Application No. PCT/US2015/010859, dated Jul. 12, 2016 (8 pages).

* cited by examiner

*Primary Examiner* — Brian Gangle
*Assistant Examiner* — Andrea K McCollum
(74) *Attorney, Agent, or Firm* — Clark & Elbing LLP

(57) ABSTRACT

Featured are methods of diagnosing and treating liver disease.

Figure 1:
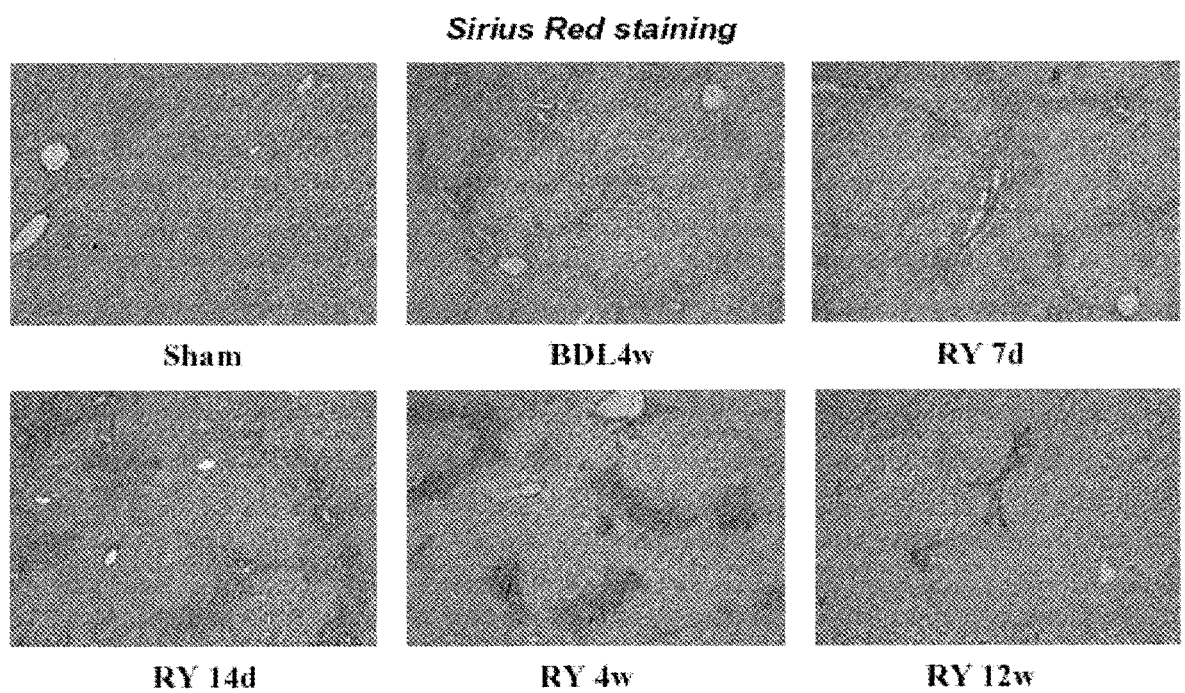

9 Claims, 8 Drawing Sheets
Specification includes a Sequence Listing.

DIAGNOSIS OF CHRONIC LIVER DISEASES

The present invention generally relates to methods for diagnosing liver diseases using protein biomarkers and to the use of biomarkers or monitoring treatment of human subjects and animals suffering from liver diseases. The invention further relates to a diagnostic test system using relevant biomarkers.

Liver diseases and especially progressive liver fibrosis entail high costs for the public health sector and are a major cause of death in civilized countries. The term liver disease or hepatic disease applies to various types of damage to or disease of the liver and include e.g. viral hepatitis, alcoholic liver disease, fatty liver disease, autoimmune, biliary, hereditary liver diseases, and chronic liver inflammation in general, all of which often lead to liver fibrosis which might irrevocably progress to cirrhosis. Cirrhosis is a state of organ damage which concurs with a substantial loss of liver function. Liver cirrhosis might also develop into decompensate form or primary carcinoma, both having high morbidity and mortality rates.

Liver fibrosis is a form of wound-healing response characterized by the excessive accumulation of extra-cellular matrix in the liver. Normal structural elements of tissues are replaced with excessive amounts of non-functional scar tissue. The more severe form of liver scarring is hepatic cirrhosis which unlike hepatic fibrosis is generally considered to be irreversible. In Europe and the USA, cirrhosis prevalence is about 250 cases per 100,000 persons per year and in the USA, it accounted for more than 25.000 deaths and 373.000 patients in hospital attendance in the year 1998 which is likely a severe underestimate.

A frequent complication of cirrhosis is liver cancer, in particular hepatocellular carcinoma (HCC). Thus, chronic hepatitis C causes HCC through the stage of cirrhosis, while in chronic hepatitis B, the integration of the viral genome into infected cells can directly induce a non-cirrhotic liver to develop HCC, while cirrhosis remains a major determinant of malignancy. Treatment options and prognosis of HCC are dependent on many factors but especially on the degree of cirrhotic decompensation, apart from tumor size and staging. Therefore, the availability of prognostic tools to find out in an early stage whether cirrhosis will develop is highly important.

It is undisputed that sequelae of cirrhosis, such as ascites and variceal bleeding due to portal hypertension, decompensation of liver function, HCC and death can be considered hard clinical endpoints. Similarly, the development of cirrhosis has been accepted as a hard endpoint, since, even if compensated, cirrhosis incurs a high risk of morbidity and mortality. Non-cirrhotic fibrosis itself, which spans the range from mild periportal (e.g. Metavir score of F1) to severe with bridging (Metavir F3), can only be considered a surrogate for progression to cirrhosis, especially for F3>F2, since mild fibrosis (F1) can regress, remain stable or may progress only slowly. Therefore, diagnosis of the extent of fibrosis, especially of significant fibrosis (F2-F3), or cirrhosis (F4) is clinically relevant, either to guide treatment decisions, to perform regular monitoring for complications, or to consider antifibrotic therapies (1-5).

Notably, the extent of fibrosis (the amount of scar tissue) in cirrhosis is not the sole determinant of the severity of liver dysfunction. It is rather the combination of fibrosis with unfavorable architectural remodeling, mainly by pathological angiogenesis that causes liver dysfunction by disconnection of hepatocytes from the portal venous blood supply via sinusoidal capillarization and portal-portal and portal-central venous shunting (1, 5-6). This is also exemplified by the variant rate of decompensation in chronic liver diseases of different etiology despite a similar extent of scar tissue formation, e.g. in biliary vs. parenchymal fibrosis. Yet, correct diagnosis of liver fibrosis stage, including the extent of scar tissue deposition, and especially assessment of fibrosis progression (fibrogenesis) remains a highly relevant if not the most relevant diagnostic and prognostic parameter in patients with liver diseases.

Within current methods to assess fibrosis and fibrogenesis, liver biopsy that uses conventional staging systems is the primary tool for the diagnosis and assessment of liver diseases. However, there are a number of well-documented limitations and disadvantages due to its invasive nature and associated stress for patients and physicians (7), but most importantly significant sampling error, even in diseases that affect the liver uniformly. Because a single liver biopsy represents only a fifty thousandths of the total organ volume, a small change in the angle of the biopsy needle can yield different staging results. Moreover, sampling error is an even greater concern in cases where the injury is more heterogeneous, such as in biliary fibrosis. Therefore, monitoring and treating patients by relying upon changes in fibrosis stage perceived through sequential liver biopsies may be misleading. To date, it is difficult or impossible to measure fibrosis progression or regression in patients since the evolution of these changes is usually slow and repeated liver biopsies within short time intervals are unethical and prone to sampling error.

Thus, in a study that compared laparoscopic liver biopsies from the right and the left lobe in patients with chronic hepatitis C that were scored in a blinded fashion, one third of paired samples differed by at least one out of the four Metavir stages, and 14.5% differed in the diagnosis of advanced fibrosis (F3) vs. cirrhosis (F4). However, a two-stage difference was rare and was only found in 3% of cases (8). Assessment of virtual liver biopsies constructed from surgical samples from patients with hepatitis C showed that even large biopsies (length >25 mm) display a one-stage variability of 25% (9). Even higher one-stage variabilities were also reported for non-alcoholic steatohepatitis NASH (40%, ref. 10) and biliary fibrosis (60%, ref. 11). Therefore, biopsy is losing ground for mere fibrosis assessment, while it remains a valuable tool to search for primary and secondary etiologies of liver disease.

Moreover, biopsy stage does not reflect the dynamics of fibrogenesis and is only a modest predictor of decompensation or death. Dynamic biopsy parameters have recently been assessed and found predictive, such as semiquantification of activated α-SMA-positive myofibroblasts and the major fibrogenic cytokine TGFβ after immunostaining (12), or by quantitative PCR quantification of transcripts that are related to fibrogenesis or fibrolysis (13). However, none of these parameters has undergone rigorous validation, and they are expected to be equally affected to sampling error as is simple staging.

In the last two decades there has been some progress in the development and clinical validation of noninvasive methods to assess liver fibrosis. These comprise serum markers and elastographic methods, and to a lesser degree radiological refinements. Two serum tests (FIBROTEST® and FIBROMETER®) and one physical method (ultrasound elastography, FIBROSCAN®) have even become standard of care and are reimbursable by health insurance e.g. in France, based on cost-benefit assessment, since they are sparing an estimated ~50% of patients liver biopsy for clinical decision making. Yet, due to biopsy sampling variability validation of biomarkers and such physical methods suffers from the lack of a real gold standard. Moreover, they have been validated mainly in patients with chronic hepatitis C and as surrogates for static fibrosis measurement, while especially the serum markers should rather reflect dynamic processes such as fibrogenesis or fibrolysis (scar tissue formation and resolution, resp.). Only recently the potential role of certain serum markers as predictors of long-term morbidity and mortality has been considered (see below).

Disappointingly, all current non-invasive methodologies yield a sufficient to excellent diagnostic accuracy for the detection (or exclusion) of advanced fibrosis and cirrhosis (F3-F4), but display low sensitivities and specificities for intermediate fibrosis stages (F1 and F2). Notably, none has been validated thoroughly for a step-wise follow-up of the fibrogenic evolution of chronic liver disease (4,5,14-17), which is particularly needed for clinical studies with potential antifibrotic agents.

For proper interpretation of the diagnostic utility of these noninvasive tests, the following points need consideration, such as 1. sufficient sample size; 2. patient sample being representative of a normal referral cohort (or even the general population when screening is intended), e.g., avoiding a high percentage of subjects with advanced fibrosis; 3. defined etiology of fibrosis; 4. and matched sampling for the novel test vs. the standard liver biopsy staging (which is still the tarnished gold standard of fibrosis). In order to correct for study and validation samples that are not representative of the general or the final target population (spectrum bias), corrective formulas such as DANA (difference between advanced and non-advanced fibrosis stages) have been applied (18).

Diagnostic accuracy is often expressed as area under receiver operating curves (AUROC, which factors in both test sensitivity and specificity and thus reflects the diagnostic precision in select populations): An AUROC of 1.0 describes a perfect test to diagnose or rule out a condition, and tests with AUROC values of 0.90 and above are considered potentially useful. For noninvasive tests of liver fibrosis, the condition to be diagnosed is usually significant fibrosis (Metavir stages F2-4) vs. no or mild fibrosis (F0-1), but other evaluations, i.e., the diagnosis of severe fibrosis (F3-4) or cirrhosis (F4) are also performed. While these relatively crude comparisons are clinically meaningful, they are less useful for studies that are aimed at assessing fibrosis progression or at testing antifibrotic agents.

Importantly, the major limitation of test validation remains the inaccuracy of the current gold standard (liver biopsy). Even in the 'best case' scenario where its presumed accuracy is highest (with a sensitivity and specificity of 90%) and the prevalence of significant fibrosis is 40%, the calculated AUROC would be 0.90 for a perfect marker or method (99% actual accuracy) which is within the range of what has already been observed with some tests. With lower biopsy sensitivity and specificity, which is the real world scenario, AUROC determinations >0.90 cannot be achieved even for a marker that perfectly measured fibrosis (19).

Conventional and contrast ultrasonography, computerized tomography and magnetic resonance (MR) imaging can aid in the diagnosis of (compensated) cirrhosis, but do not detect lower stages of fibrosis. Positron emission tomography (PET), single photon emission computerized tomography (SPECT) and diffusion-weighted MRI do not add significant information. While promising, double contrast MRI that uses supra-paramagnetic iron and gadolinium as contrast agents was abandoned due to side effects. Currently, only MR texture analysis which requires sophisticated instrumentation and software may permit semiquantitative fibrosis assessment (4,20-21).

Ultrasound elastography (UE) is a noninvasive bedside method to assess liver fibrosis by measuring hepatic stiffness. A probe is placed intercostally and transmits low amplitude shear waves though the liver. Longitudinal share wave velocity is determined by an integrated pulse-echo ultrasound and is correlated with liver stiffness. UE is painless and can be performed in a standardized way after short training. Means of 10 acquisitions are calculated and the procedures only takes 5-10 min. Compared to biopsy, UE samples a ~100-fold larger volume (~1/500 of the liver), potentially reducing sampling variability. More than 300 clinical studies correlating ultrasound elastography with liver biopsy have appeared since its first description in 2003, including meta-analyses and a recent comprehensive review (2). Liver stiffness values (in kPa) correlate well with histological fibrosis, and AUROC curves yield excellent accuracy for diagnosing HBV or HCV cirrhosis from non-cirrhosis (AUROC between 0.85 and 0.97), but lower accuracy for significant fibrosis (F2) (AUROC between 0.78 and 0.97) (2). Diagnosis of cirrhosis in other etiologies requires different cut-offs, but yields similar accuracy which is particularly important for e.g. biliary fibrosis where biopsy sampling variability is high. On the other hand, severe inflammation and mechanical cholestasis must be factored in, since they can significantly increase hepatic stiffness, thus confounding the fibrosis readout. UE has proven useful for diagnosis of (compensated) cirrhosis, the prediction of complications of cirrhosis and for (pre-biopsy) stratification of patients for inclusion into clinical studies (2,4,14).

Axial radiation force imaging (ARFI or shear wave elastography) measures the velocity of higher frequency shear waves that spread perpendicularly to the acoustic push pulse. Displacement velocity is proportional to tissue stiffness. An advantage of ARFI vs. UE is that it permits simultaneous B-mode real time ultrasound, including selection of a suitable area in the liver (other than the mere transcostal approach of UE). Moreover, it can be added to a conventional B-mode US-scanner. A disadvantage is the smaller volume of tissue sampled and a narrower range of velocities that differentiate between normal, fibrotic and cirrhotic liver, which led to the conclusion that ARFI is slightly less diagnostic than UE. However, a recent single center study from Italy that compared UE and ARFI with biopsy staging in 121 patients with chronic hepatitis C showed superiority of ARFI for the differentiation of F0-F1 versus F2-F4, F0-F2 versus F3-F4, and F0-F3 versus F4, reaching AUROC values of 0.92, 0.98, 0.98, and 0.96, resp. (22). This suggests that recent ARFI developments are promising.

MR elastography (MRE) employs similar principles as UE/ARFI, and radial shear wave velocity is recorded with a 1.5 Tesla MR scanner (4,20). While the means and skills to operate MRE are not yet generally available, it does not require contrast application and offers other advantages over UE or ARFI, such as examination of the whole liver, and applicability in patients with ascites, severe obesity or narrow intercostal spaces. Moreover, acquisition times can now be shortened to 2 min by use of echo-planar vs. spin-echo sequences, without compromise of the stiffness readout. A larger comparative study in 96 patients from Belgium with different liver diseases demonstrated high precision to diagnose histological fibrosis F2, F3, and F=4 (AUROC 0.994, 0.985, and 0.998, resp.) (23). However, in view of the sampling variability of biopsy, these data need to be reproduced. Moreover, as with UE and ARFI hepatic inflammation and mechanical cholestasis can confound results of MRE.

Recently, a high number of studies were published that employed serological markers and especially their combinations to cross-sectionally stage liver fibrosis (reviewed in 1,14-17,24,25). These tests have largely been used in chronic hepatitis C but more studies in other liver diseases are emerging. Serum parameters either reflect liver inflammation and function (indirect markers), are related to matrix metabolism (direct markers), or incorporate both categories. The best panels usually show diagnostic accuracies (AU-ROCs) around 80-85% for the dichotomous differentiation between no or mild (Metavir F0/1) and moderate-severe (Metavir F2-4), or between mild-moderate (Metavir 0-2) and severe (Metavir 3-4) fibrosis. In view of the normally slow fibrosis progression, their inability to differentiate adjacent and intermediate fibrosis stages, e.g., stage 1 from 2, or stage 2 from 3, and the high proportion of indeterminate values with an inability to stage fibrosis in 30-70% of patients with intermediate fibrosis stages, should preclude their use as surrogates in clinical studies with potential antifibrotics. On the other hand, they are functionally dynamic parameters that are (inappropriately) used to stage a static condition, i.e. the extent of fibrosis (fibrosis stage). Finally, fibrosis progression is nonlinear, with faster progression at advanced stages and roughly a doubling of scar tissue for each stage proceeding from F1 to F4 (9,26). As mentioned above, a major obstacle to further improve on serum biomarkers for exact fibrosis staging is the lack of a real gold standard, with current reliance on matched liver biopsy.

While the fibrosis markers have almost exclusively been validated as predictors of fibrosis stage, particularly the direct (matrix related) parameters may rather reflect dynamic alterations, i.e., fibrogenesis and/or fibrolysis. Fortunately, several recent studies suggest that certain marker combinations, such as the FIBROTEST®, and especially the enhanced liver fibrosis panel (ELF) have a high predictive value for severe outcome or death in long term (retrospective) follow-up studies of patients with chronic hepatitis C or PBC (27-31). Notably, prognostic value appears to be superior to the predictive power of histological fibrosis stage, the Child-Pugh or the MELD score. However, their validation as dynamic markers of fibrogenesis is difficult and will require more long term and intervention studies, e.g. validation in trials with potential antifibrotics that use a broad panel of optimized histological, serological and imaging readouts (4,5). Final proof will only be possible with the development of quantitative imaging of hepatic fibrosis and fibrogenesis as novel gold standard.

A functional parameter that is correlated with the extent of remodeling in cirrhosis and that serves as a good predictor of hard endpoints is the hepatic-portal vein pressure gradient (HVPG) (32,33). Since this test which can be performed with high reproducibility is invasive and only carried out in a few centers, a non-invasive and easy-to-perform HVPG measurement is urgently needed. A recent study showed that this may be possible. Thus the "hepatic vein arrival time" of an ultrasound contrast agent can detect the clinically relevant increased HVPG10 mm Hg with high accuracy (AU-ROC of 0.973) (34).

Nonradioactive $^{13}$C-labelled breath tests were proposed for the evaluation of human liver function >30 years ago, and are currently reconsidered as a valuable asset to monitor the metabolic capacity of the liver, e.g. in studies with antifibrotics. Tests of microsomal liver function, which measure mainly the activity of several cytochrome P450 species in hepatocytes, are preferred over those of cytosolic or mitochondrial function (35). One of the best examined tests is based on demethylation of ingested methacetin and quantification of the exhaled metabolite $^{13}CO_2$. It is largely independent of liver perfusion and $^{13}CO_2$ correlates inversely with the severity (inflammation and fibrosis) of chronic liver diseases. However, microsomal enzyme induction by, e.g., active smoking, certain drugs or excessive consumption of ethanol, as well as active NASH can increase exhaled $^{13}CO_2$ levels. Therefore, these confounders have to be ruled out in clinical studies.

Quantitative (targeted) imaging employs a high affinity ligand for a cell associated molecule or a matrix structure that has been coupled to a radio- or MRI-imaging agent (4). The imaging agent should be small to permit good tissue penetration, have a low unspecific uptake by e.g. Kupffer cells or hepatocytes, and yield a plasma half life in the range of 10-30 min, with predominant elimination through the kidneys. The target molecules of choice to image fibrosis are the abundant fibrillar collagens. Possible targets for imaging fibrogenesis are cell surface markers that are exclusively upregulated on fibrogenic cells, such as the cholangiocyte integrin $\alpha v \beta 6$ and the myofibroblast-specific PDGF$\beta$R (4). The availability of quantitative fibrogenesis imaging over the whole liver could permit testing of antifibrotic agents in small numbers of patients and over short periods of time. If reliable, such methodology could serve as novel gold standard for the validation of fibrosis/fibrogenesis serum markers and serum marker panels.

The most promising approach to develop novel serum markers of fibrosis, fibrogenesis and fibrolysis is the use of well defined rodent models of fibrosis progression or reversal that permit correlation of serum markers with, e.g., collagen content (fibrosis) and transcript levels related to fibrogenesis or fibrolysis in matched liver tissue. This is presently in development. Novel markers then need to be further validated in patients (4).

Microparticles are small cell membrane vesicles that are released from activated or apoptotic cells. They carry internal and cell surface molecules from their parent cell which allows their identification and quantification in the blood stream. They promise to open a novel diagnostic armamentarium to monitor cell specific activation and apoptosis in liver inflammation and fibrosis (36).

Similarly, circulating micro-RNA, which is at least in part contained in microparticles, can reflect liver-specific pathology, including hepatocyte differentiation, activation and HCC, and possibly liver fibrosis (37).

Improved and reliable methods for quantification of fibrosis and fibrogenesis are emerging. A major problem is the current lack of a gold standard. Exact assessment of fibrosis and fibrogenesis gains increasing importance for clinical studies aimed at antifibrotic drug development and for an individualized medicine.

Even considering the recent developments with regard to diagnosis and monitoring of liver diseases, there is still an even increasing need for the development of reliable diagnostic tools and methods which can be used for the exact diagnosis of the extent of fibrosis and especially also for measurement of fibrosis progression (i.e., fibrogenesis) or regression (i.e., fibrolysis) of (fibrotic) liver disease with or without (antifibrotic) therapy. To fulfill such requirement, useful biomarkers need to be particularly sensitive and able to reflect the current disease stage and activity in a dependable manner. It was therefore an object of the present invention to provide a non-invasive diagnostic system based on such sensitive biomarkers that accurately reflect the various stages of hepatic fibrosis but also measure fibrogenesis and/or fibrolysis. Such markers are considered to be invaluable assets for the diagnosis and the monitoring of liver diseases in patients.

To solve this object, as a first subject matter the present invention provides a method of diagnosing a liver disease, comprising the steps of:

a) obtaining a biological sample from a human or animal subject, b) determining one or more biomarkers that are associated with said liver disease, c) measuring the level of said one or more biomarkers in said biological sample, d) comparing said level of said one or more biomarkers to a control level of said one or more biomarkers, and e) providing a treatment for said liver disease in said patient if a differing level of at least one of said one or more biomarkers has been detected based on analyzing the above steps, wherein said biomarker is a protein or a peptide fragment thereof selected from the group consisting of: Kininogen-1, Nesprin-1, Vitronectin, Nieman-Pick C1-like protein 1, Protocadherin Fat 4, Probable E3 ubiquitin-protein ligase HERC2, Extracellular matrix protein FRAS1, E3 ubiquitin-protein ligase UBR3, WD repeat-containing protein 90, Ephrin type-B receptor 3, Probable E3 ubiquitin-protein ligase MYCBP2, Transient receptor potential cation channel subfamily M member 4, Protein FAM71 B, WD repeat-containing protein 85, E3 ubiquitin-protein ligase UBR2, Transmembrane protein 206, Mucin-6, Myotubularin-related protein 9, Nick-associated protein 1, vesicular glutamate transporter 2, Arf-GAP with GTPase, ANK repeat and PH domain containing protein 3, Slit homolog 2 protein, Beta-1,3-galactosyl-O-glycosyl-glycoprotein beta-1,6-N-acetyl-glucosaminyltransferase 7, Fibronectin type III domain containing protein 3C1, and Homeobox even-skipped homolog protein 1, a nucleic acid encoding said protein, or a microRNA specifically regulating the expression of said protein at an RNA level.

During their studies, the inventors were able to determine that the expression of several unique proteins, i.e. the above enumerated proteins, is dysregulated in patients with liver diseases. The inventors further discovered that these proteins are differentially expressed in samples from patients affected with liver diseases and especially with chronic liver diseases when compared with healthy individuals.

Within the context of the present invention, the terms "human or animal subject" and "patient" are used synonymous and are intended to encompass human and animal subjects which are suspected of developing, are developing or have developed a liver disease. Both humans and animals (from here on termed "patient") can be subjected to the inventive methods and test systems.

In body fluids, as in particular in the serum of the patients, there are different amounts of the different proteins, depending on the disease state of the patient which is why these proteins can be beneficially used as new biomarkers for liver diseases. Within the framework of the work leading to the present invention it could be established that the levels of these proteins in body fluids of patients, especially in serum, correlate surprisingly accurately with the stage of hepatic fibrosis which was determined e.g. using the Metavir standard or quantitative collagen determination from liver biopsy, or with hepatic fibrogenesis or fibrolysis.

In particular, it was observed that in the early stage of a liver disease, with mild or modest fibrosis, there are different levels of the specific biomarkers present in patients' body fluids as compared to a later stage, i.e., advanced fibrosis or cirrhosis or during the transformation to liver cancer. Moreover, certain markers were high during active fibrogenesis, even in low fibrosis stages, or increased during fibrolysis but not during fibrogenesis. Thus, the determination of at least one biomarker as defined above allows to exactly classify the patient's disease state as mild fibrosis, more severe fibrosis, cirrhosis, or cirrhosis and HCC, whereas other biomarkers reflected the activity of progression or reversal. Since the inventive biomarkers are highly sensitive and level-wise closely correlated with the progression of liver diseases, a particularly differentiated diagnosis becomes possible.

In the method of the present invention for diagnosing a chronic liver disease, the level of a biomarker determined in a sample from a patient is compared to a control level of said biomarker. The term "control level" refers to reference biomarker data in patients without liver disease or without fibrogenic liver disease, as can be determined by any suitable method.

In one embodiment, the control level is based upon data relating to one or more comparative human or animal subjects other than the diagnosed patients, preferably healthy subjects as well as subjects with otherwise reliably diagnosed liver disease of various stages. In another embodiment, the control level is based upon data previously obtained from the diagnosed patient and is optionally also based on data obtained from one or more other subjects.

The term "fibrosis" refers to any of a variety of biological phenomena that are characteristic of a fibrotic cell. The phenomena can vary with the type of fibrosis but the fibrosis phenotype is generally identified by abnormalities in scar tissue formation.

The terms "diagnosis" and "diagnosing" generally include a determination of a subject's susceptibility to a disease or disorder, a determination as to whether a subject is presently affected by the disease or disorder, a prognosis of a subject affected by a disease or disorder and monitoring a subject's condition to provide information as to the effect or efficacy of therapy.

In terms of the present invention, the term "biomarker" refers to the above proteins which were found to be differentially expressed in patients affected with liver diseases as well as to the respective nucleic acid encoding these proteins. The diagnosis of a chronic liver disease can be made by means of determining in a biological sample taken from the human or animal subject the amount of at least one of the mentioned proteins or in the alternative by determining the amount of a nucleic acid encoding said protein. In terms of the present invention, nucleic acids encoding the protein biomarkers of the invention are particularly designated as "nucleic acid biomarkers". The nucleic acid biomarkers encoding a protein biomarker of the present invention can further include regulatory sequences, e.g. a promoter, enhancer and so forth.

Also encompassed by the term "biomarker" according of the present invention are peptide fragments of the respective proteins which can also be detected and correlated with the level of the complete protein or peptide fragment thereof in healthy individuals to provide the required data for a fibrosis staging. Further, the term "biomarker" is intended to encompass microRNA which specifically regulates the expression of the biomarker proteins on an RNA level. Also the determination of the levels of such microRNA can provide the required information about the levels of such proteins in a patient and accordingly about the disease state.

Among the above mentioned group of biomarker proteins there are proteins which have proven to be especially suitable as biomarkers and results of tests performed using these proteins are especially sensitive and reliable. Accordingly, in a first preferred embodiment of the present invention, the method according to the present invention uses as biomarker proteins especially in view of determining fibrolysis one or more of Transmembrane protein 206, Kininogen-1, E3 ubiquitin-protein ligase UBR3, Mucin 6, Nesprin-1, Protein FAM71B, Arf-GAP with GTPase, ANK repeat and PH domain-containing protein 3, E3 ubiquitin-protein ligase UBR2, Probable E3 ubiquitin-protein ligase HERC2, WD repeat-containing protein 85, Niemann-Pick C1-like protein 1, Probable E3 ubiquitin-protein ligase MYCBP2, Protocadherin Fat 4, Extracellular matrix protein FRAS1 and Vitronectin. Among these biomarker proteins an especially preferred selection for use as the one or more biomarkers are the group of proteins including Transmembrane protein 206, Kininogen-1, E3 ubiquitin-protein ligase UBR3, Mucin 6, Nesprin-1 and Protein FAM71B.

In a second preferred embodiment of the present invention, the method according to the present invention uses as biomarker proteins especially in view of determining fibrogenesis one or more of Ephrin type-B receptor 3, WD repeat-containing protein 90, Transient receptor potential cation channel subfamily M member 4, Homeobox even-skipped homolog protein 1, Slit homolog 2 protein, Myotubularin-related protein 9, Nck-associated protein 1, Fibronectin type III domain containing protein 3C1 and Vesicular glutamate transporter 2. Among these biomarker proteins an especially preferred selection for use as the one or more biomarkers are the group of proteins including Ephrin type-B receptor 3, WD repeat-containing protein 90, Transient receptor potential cation channel subfamily M member 4, Homeobox even-skipped homolog protein 1, Slit homolog 2 protein and Myotubularin-related protein 9.

It is particularly preferred for the method of the present invention to determine at least three of the above biomarkers. The determination of three or more biomarkers enables a particularly precise evaluation of the disease state of the patient. The more of these biomarkers are used for analyzing the disease state of a patient, the better the result will correlate to the actual condition of the patient. It is therefore even more preferred to perform the method according to the invention using at least five and especially preferred using ten or more of the above mentioned biomarker proteins, nucleic acids or microRNAs. Limits to the use of an even higher number of biomarkers might be arising because of cost-benefit considerations.

A "biological sample" in terms of the present invention may be any of a variety of sample types obtained from an organism that may be used in a diagnostic assay.

The term encompasses body fluids such as blood, serum, plasma, urine and other liquid samples from biological origin, solid tissue samples such as biopsy specimen or tissue cultures or cells derived therefrom and the progeny thereof. Additionally, the term may encompass circulating tumor or other cells. The term specifically encompasses a clinical sample and further includes cells in cell culture, cell supernatants, cell lysates, serum, plasma, urine, amniotic fluid, biological fluids and tissue samples. The term also encompasses samples that have been manipulated in any way after procurement such as treatment with reagents, solubilization or enrichment for certain components. All of such sample specimen can be used within the method of the present invention as long as they allow to determine the level of the biomarkers mentioned herein as their presence therein allows a correlation with liver diseases.

In a second aspect, the present invention provides a method for monitoring a disease state of a patient affected with a liver disease, comprising:

a) determining the level of at least one biomarker in a biological sample obtained from a patient at a first point in time, b) determining the level of the at least one biomarker of step a) in a biological sample obtained from the patient at a second point in time, and c) comparing the results obtained in steps a) and b), wherein an altered level of said at least one or more biomarkers when comparing the results obtained in step a) and b) indicates an improvement or an aggravation in said disease state, and the biomarkers are defined as above for the method of diagnosing a liver disease.

Due to their high precision according to which the biomarkers of the present invention allow a determination even in view of the disease stage of the patient who suffers from a liver disease (preferably a chronic liver disease), it is possible to exactly monitor as to how the patient's state changes over time. Thus, it is possible to monitor whether the condition improves, e.g., as a consequence of a therapeutic intervention, whether a certain medication or measure has a positive effect or whether the condition gets worse over time. In this context, the inventors found out that the biomarkers quickly reflect changes in view of the patient's state and allow an early statement as to how the state changes, i.e. improves or deteriorates. Accordingly, a medical treatment or the management of a liver disease is preferably adjusted according to the determination of levels of the one or more biomarkers in the biological sample of the patient.

A third aspect and still further subject matter of the present invention is a diagnostic test system which allows for the diagnosis or monitoring of patients with liver diseases. The diagnostic test system comprises one or more detecting agents which specifically bind to one of said one or more biomarkers, wherein each of said one or more biomarkers is a protein or a peptide fragment thereof selected from the group consisting of: Kininogen-1, Nesprin-1, Vitronectin, Nieman-Pick C1-like protein 1, Protocadherin Fat 4, Probable E3 ubiquitin-protein ligase HERC2, Extracellular matrix protein FRAS1, E3 ubiquitin-protein ligase UBR3, WD repeat-containing protein 90, Ephrin type-B receptor 3, Probable E3 ubiquitin-protein ligase MYCBP2, Transient receptor potential cation channel subfamily M member 4, Protein FAM71 B, WD repeat-containing protein 85, E3 ubiquitin-protein ligase UBR2, Transmembrane protein 206, Mucin-6, Myotubularin-related protein 9, Nick-associated protein 1, vesicular glutamate transporter 2, Arf-GAP with GTPase, ANK repeat and PH domain containing protein 3, Slit homolog 2 protein, Beta-1,3-galactosyl-O-glycosyl-glycoprotein beta-1,6-N-acetyl-glucosaminyltransferase 7, Fibronectin type Ill domain containing protein 3C1, and Homeobox even-skipped homolog protein 1, a nucleic acid encoding said protein, or a microRNA specifically regulating expression of said protein at an RNA level.

All definitions and explanations made above with regards to the diagnostic method of the first aspect of the invention equally apply to the method of monitoring the disease state and the diagnostic test system according to the second and third aspects of the invention. Also the following explanations about the preferred further embodiments for the methods and test system likewise apply to all the subject matters of the present invention.

Preferred sets of biomarkers as described above for determining fibrolysis or fibrogenesis equally apply to the diagnostic test system described here.

The determination of the level of the biomarkers of the present invention can be affected by any common methods known in the art. A quantitative determination may therefore, for example, involve binding of a specific binding agent to a biomarker and measuring a signal obtained in response to the specific binding. Also the above mentioned radio- or MRI-imaging methods (4) can be used for the determination of the level of the biomarkers in the biological sample or in the liver or any other organ prone to fibrosis in general.

Within the gist of the invention, the diagnostic test system can comprise just one detecting agent for one biomarker to be determined or it may contain different detecting agents for each of the more than one biomarker to be detected in different compartments or part of the kit, or in the alternative different detecting agents can be present in one and the same compartment or part of the test system.

In a preferred embodiment of the invention, the test system further comprises one or more binding agents which are preferably bound to or capable to be bound to a solid support, and the system can contain e.g. only one solid support with one or more binding agents bound thereto.

According to a preferred embodiment of the invention, the one or more detecting agents contain a detectable label or are conjugated with a detectable label. In case of nucleic acid biomarkers, preferred binding partners are nucleic acids capable of hybridizing with the nucleic acid biomarkers.

Detecting agents in terms of the present invention may further include a detectable label. The examples of labels that have proven to be useful include radioactive elements, enzymes, fluorescent, phosphorescent and chemiluminescent dyes, latex and magnetic particles, dye crystallites, gold, silver and selenium colloidal particles, metal chelates, co-enzymes, electroactive groups, oligonucleotides, stable radicals and others.

Suitable detecting agents for determining protein biomarkers are e.g. biomarker-specific antibodies or fragments thereof. Also other affinity ligands for e.g. phage display or similar assays are encompassed within the present invention as embodiments of the term "detecting agent".

A suitable detecting agent for determining a nucleic acid biomarker is for example a nucleic acid capable of hybridizing with the nucleic acid biomarker of the present invention. For example, the presence of a nucleic acid biomarker can be detected by DNA-DNA or DNA-RNA hybridization or amplification using probes or fragments of polynucleotides encoding a protein biomarker of the present invention. Means for producing labeled hybridization probes for detecting nucleic acid biomarkers include oligolabeling, nick-translation, end-labeling or PCR amplification using a labeled nucleotide.

"Immuno assays" determine the presence of a protein biomarker in a biological sample by reacting the sample with an antibody or fragment thereof that binds to the protein biomarker, the reaction being carried out for a time and under conditions allowing the formation of an immuno complex between the antibody or fragment and the protein biomarker. The quantitative determination of such an immuno complex is then performed.

"Antibody" means any antibody including polyclonal and monoclonal antibodies or any fragment thereof that binds to a protein biomarker of the present invention. Monoclonal and/or polyclonal antibodies may be used in the methods and systems of the invention. The term "antibody" as used herein includes a whole immunoglobulin that is either monoclonal or polyclonal as well as immuno-reactive fragments that specifically bind to the protein biomarker, including fab, fab', fab" and fv, single chain fragments (scFv), single domain antibodies or the like. The term "antibody" also includes binding proteins, especially hyaluronic acid binding protein (HABP). Preferred protein biomarker antibodies are described hereinafter.

Antibodies used in preferred embodiments of the present invention can be prepared by techniques generally known in the art and are typically generated to a sample of the protein biomarkers either as an isolated naturally occurring protein, as a recombinantly expressed protein or a synthetic peptide representing an antigenic portion of the natural protein.

In one aspect, the antibody used is an antibody generated by administering to a mammal (e.g. rabbit, goat, mouse, pig, etc.) an immunogen that is a protein biomarker as described above or an immunogenic fragment thereof.

A sandwich immuno assay format may be e.g. used wherein a binding agent as described above is used to immobilize the biomarker to a solid surface and a detecting agent as described above and preferably comprising a detectable label is used to determine the amount of biomarker which is bound to the solid surface. As binding agent and as detecting agent, two antibodies can be used which bind to different epitopes of the biomarker.

The test system of the present invention therefore comprises preferably other constituents for the performance of in vitro-assays, preferably immuno assays or hybridization assays, and especially preferred an Enzyme Linked Immunosorbent Assay (ELISA) assay.

In an immuno assay, antibodies or antibody fragments are usually used which are associated with a detectable label. A large variety of labels has proved to be useful including radioactive elements, enzymes, fluorescent, phosphorescent and chemiluminescent dyes, latex and magnetic particles, dye crystallites, gold, silver and selenium colloidal particles, metal chelates, co-enzymes, electroactive groups, oligonucleotides, stable radicals and others. Such labels serve for the detection and quantification of binding events either after separating free and bound labeled reagents or by designing the system in such a way that a binding event effects a detectable change in the signal produced by the label.

The assays used in the invention can be used to determine a biomarker in any biological samples as defined above, including body fluids such as blood plasma, serum, urine, peritoneal fluid or lymphatic fluid or solid tissue samples.

Any other assay format depending on the biomarker in question and the accordingly selected detecting agents and/or binding agents can be used according to the present invention.

Automated test systems have been developed which can also be used beneficially within the context of the present invention. For example, test systems like CENTAUR® (Siemens AG), ARCHITECT™ (Abbott Diagnostics Deutschland), ELECSYS® and CLINCHEM® (both Roche) can be used and the methods and test systems of the present invention adapted accordingly.

The present invention is further illustrated by the examples below.

The attached Figures show the following:

FIG. 1: Connective tissue staining (Sirius Red) of livers of rats 4 weeks after sham operation (n=8), with BDL for 4 weeks (BDL4w, n=6), and 7, 14 days, 4 and 12 weeks after biliary drainage by RY anastomosis (RY3d: n=4, RY7d: n=6, RY14d: n=6, RY4w and RY12w: n=6). Shown are representative sections for each group.

Figure 2A:
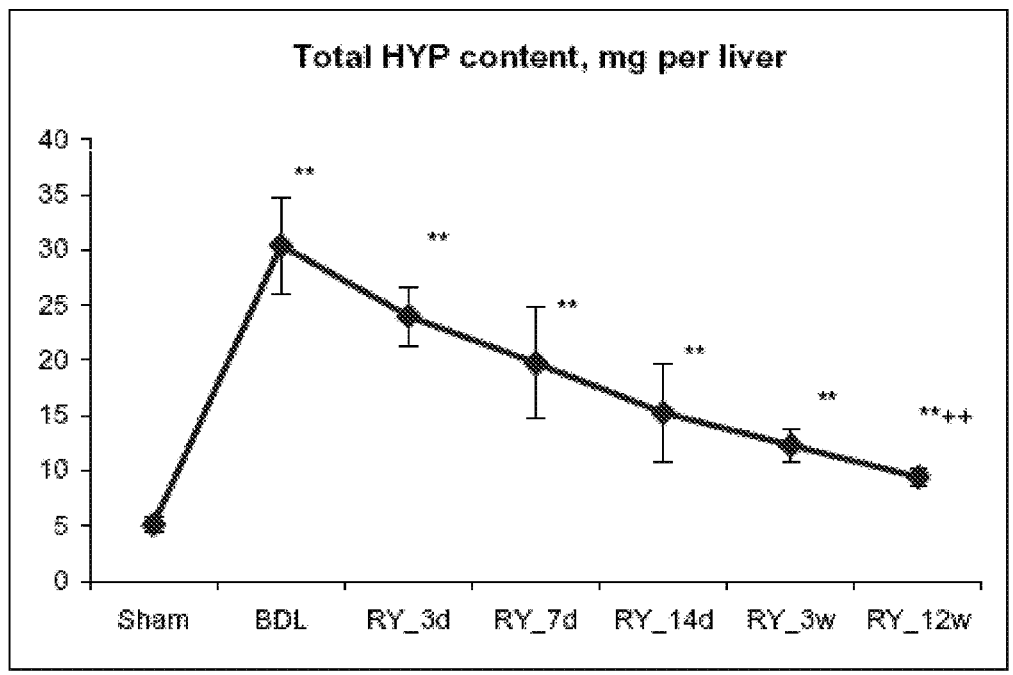
Figure 2B:
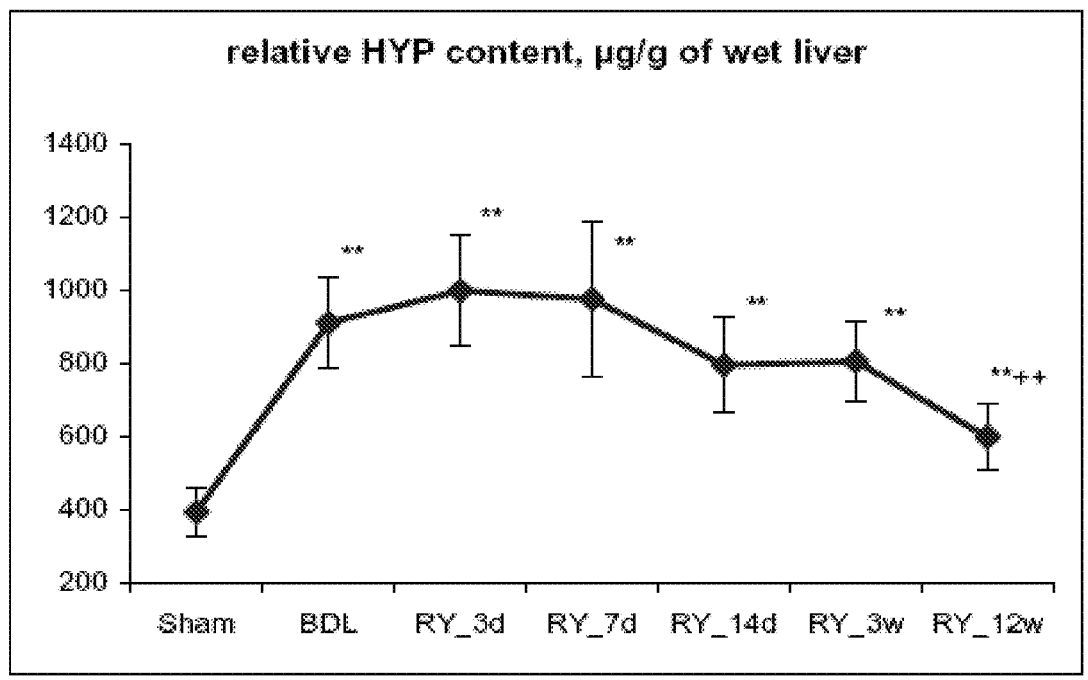

FIGS. 2A-2B: Dynamics of hepatic fibrogenesis and fibrolysis as determined by total (per liver) and relative (mcg/g of liver) collagen content in livers of the rats described in FIG. 1. *p<0.05 compared to the sham-operated group; ±p<0.05 compared to the peak fibrosis group (BDL4w). Collagen deposition was determined biochemically as hydroxyproline (HYP) in pooled representative samples from the right and the left liver (250 mg).

Figure 3A:
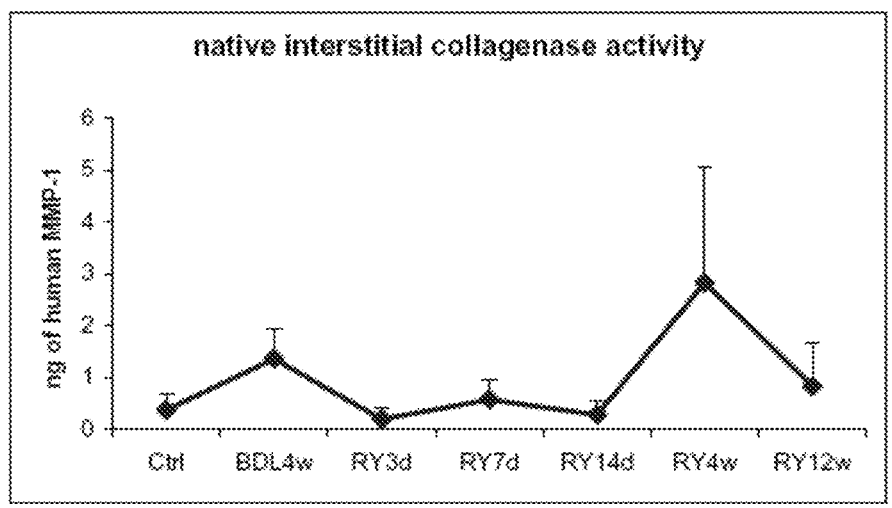
Figure 3B:
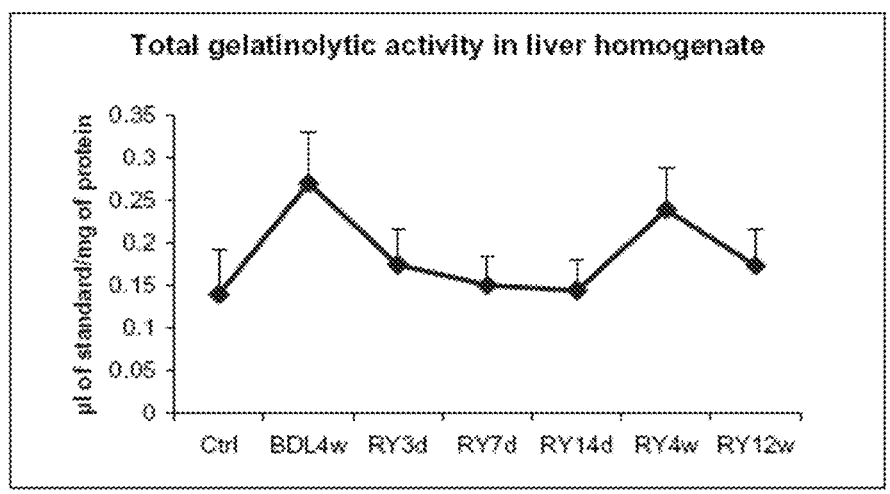

FIGS. 3A-3B: Dynamics of collagenase (FIG. 3A) and gelatinase (FIG. 3B) activities in liver homogenates during fibrosis resolution in rats after BDL (BDL4w), and 3, 7, 14 days, 4 and 12 weeks after RY-anastomosis. Protease activities were determined via collagen fragment release from biotinylated gelatin and native collagen type I, resp.

Figure 4:
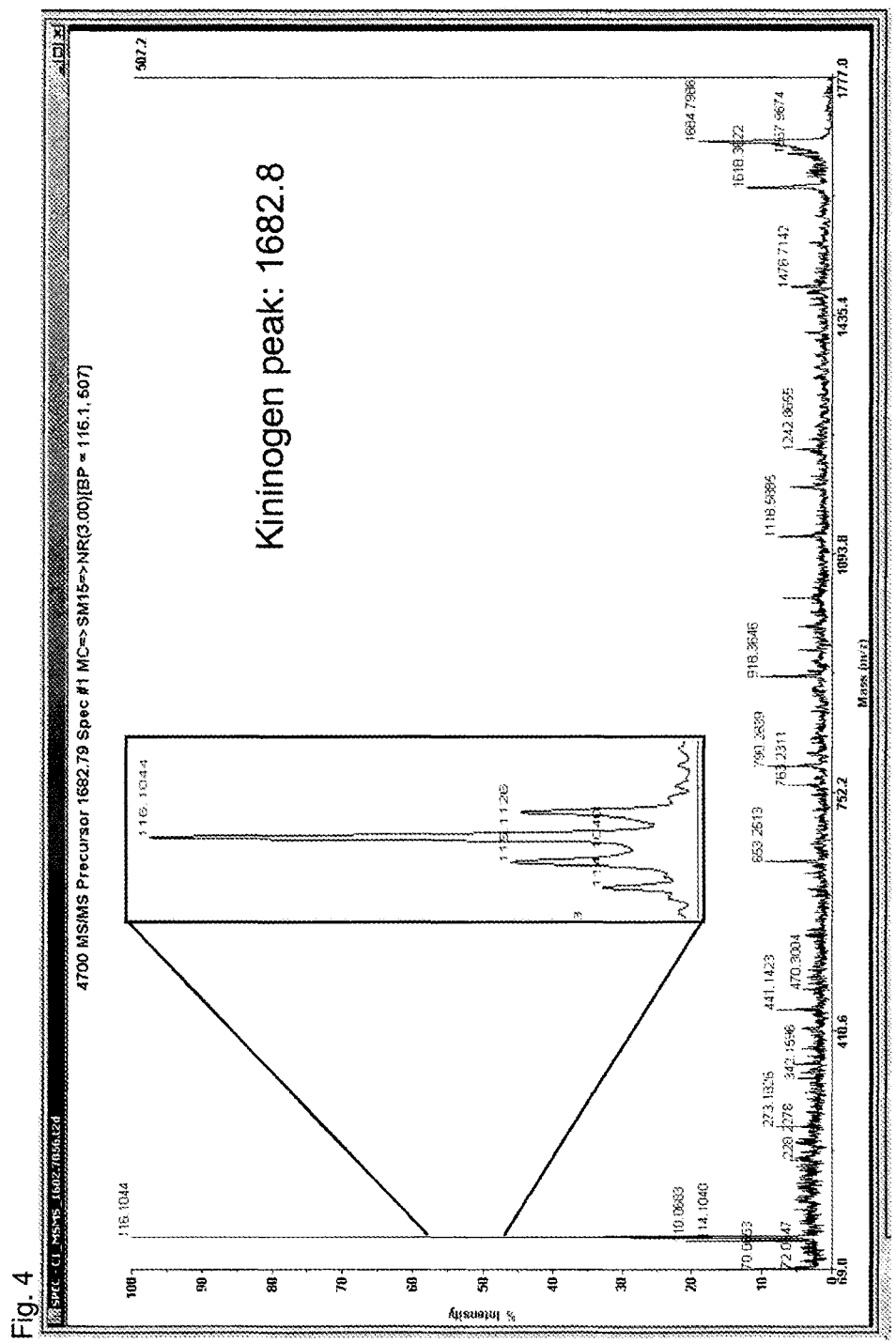
Figure 5A:
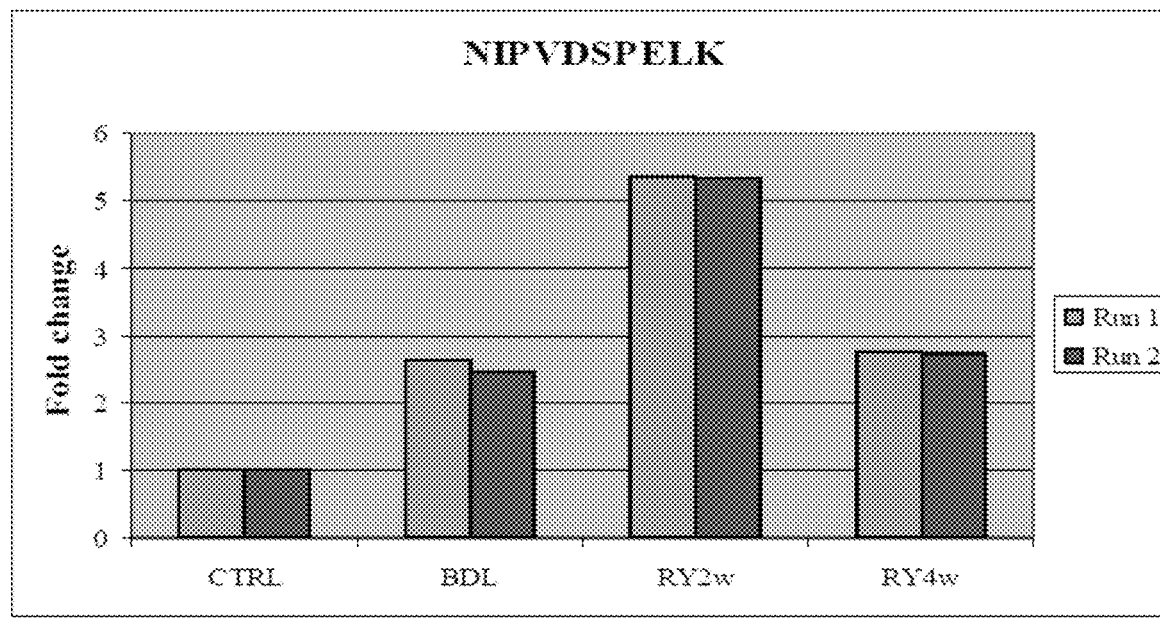
Figure 5B:
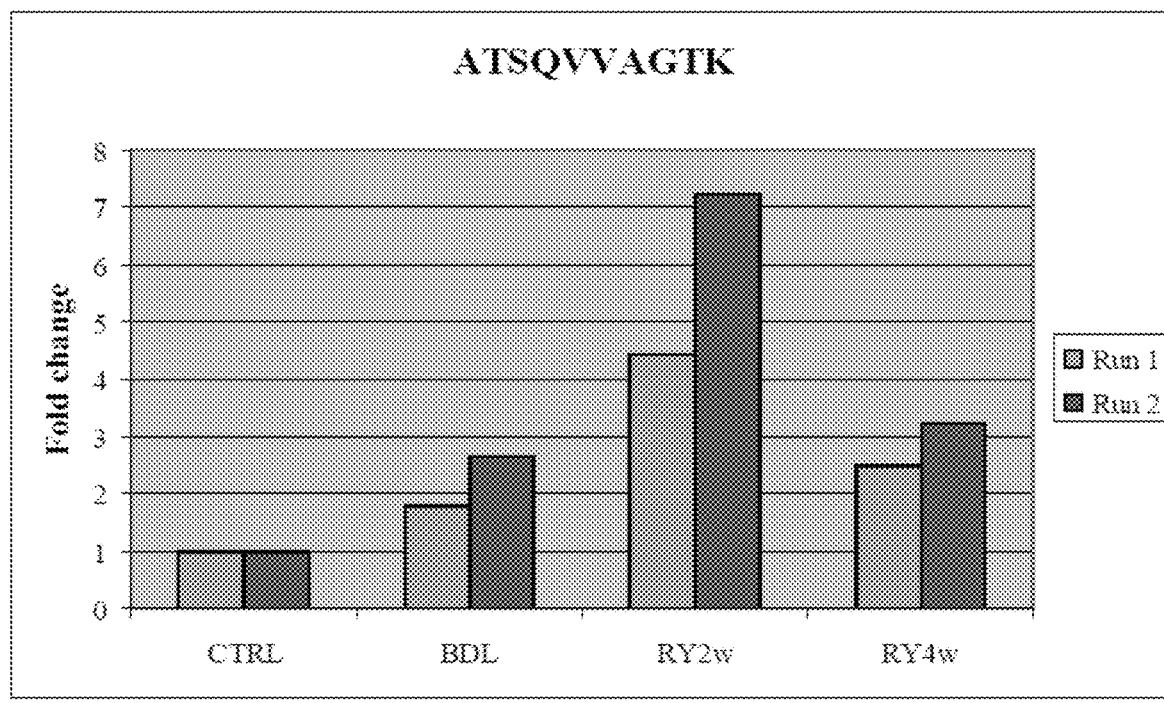
Figure 5C:
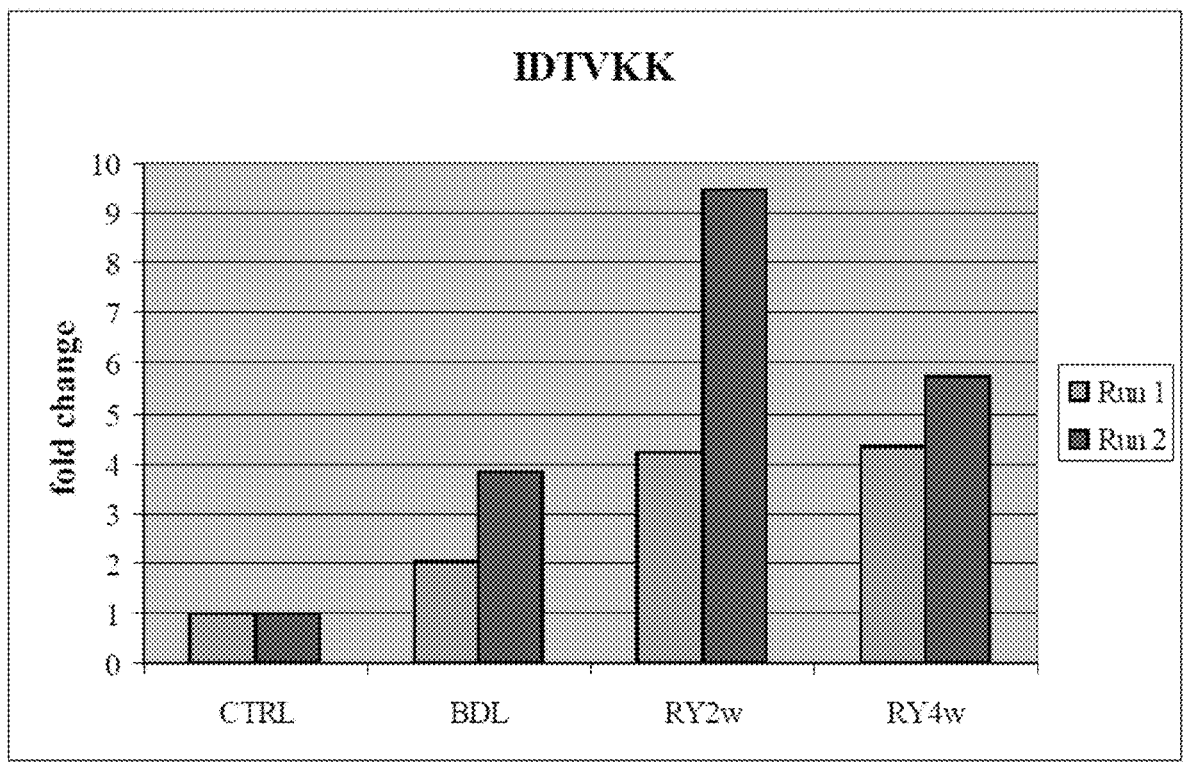

FIG. 4: A MS/MS fragmentation mass spectrum and the relative ratio of a four ITRAQ® tag system for certain detected peptides FIGS. 5A-C: Selected kininogen 1 peptides (SEQ ID NOS: 1-3), respectively) detected by ITRAQ® in two independent experiments. Run #1 was performed for pool A and run #2 for pool B, each derived from equal amounts of 3-4 sera representing half of each experimental group (n=6-8). Arbitrary units, x-fold difference compared to healthy controls (CTRL). (FIG. 5A SEQ ID NO: 1, FIG. 5B SEQ ID NO: 2, FIG. 5C SEQ ID NO: 3).

Figure 6:
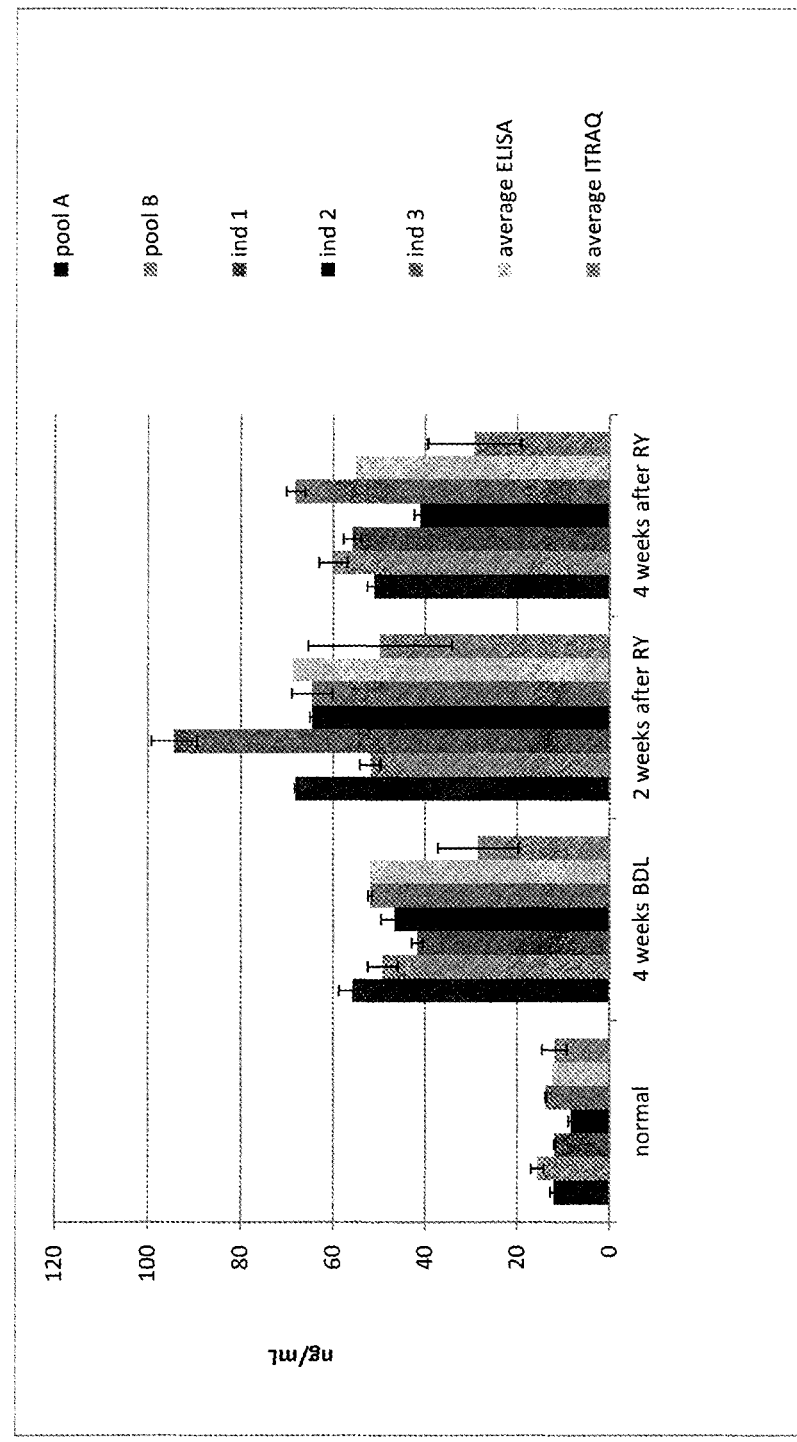

FIG. 6: Levels of kininogen 1 in two different serum pools A and B, each pooled from 3-4 sera of each condition, and from the three individual sera of pool A. Values are means±SEM of 3 determinations.

Serum kininogen 1 levels correlate well with the average ITRAQ®-MS/MS signals for the various kininogen 1 peptides.

EXAMPLE INTRODUCTION

Perpetuation of the normal hepatic wound healing response leads to liver fibrosis which often progresses to cirrhosis. In the USA cirrhosis prevalence is estimated at 0.15% or 400,000, where it accounted for more than 25,000 deaths and 373,000 hospital discharges in 1998. Fibrosis and cirrhosis result from a dysbalance of fibrolysis (removal of matrix) in favour of fibrogenesis (deposition of matrix). To date it is difficult or impossible to measure fibrosis progression or regression in patients, since evolution of these changes is usually slow and repeat liver biopsies within short time intervals are unethical and prone to sampling error. The current lack of sensitive parameters of hepatic fibrogenesis and fibrolysis has impeded antifibrotic drug development. While efforts are underway to develop non-invasive parameters that reflect the stage of hepatic fibrosis, the discovery of serum markers of fibrogenesis or fibrolysis is difficult. In this invention we identified such markers using serum proteomics. Our strategy to succeed is based on our following data: 1. Rats with bile duct ligation progress to biliary (portal) cirrhosis within 4-6 weeks, but their livers reverse to near normal within 12 weeks after biliodigestive anastomosis. 2. Progression and reversal of cirrhosis in this and related fibrosis models is associated with characteristic temporal hepatic expression patterns of fibrogenic or fibrolytic transcripts and proteins. 3. Serum proteomics of rats with portal fibrosis show distinctive peaks associated with progression or reversal. 4. Identified fibrolysis parameter(s) could already be confirmed by a serum ELISA.

Based on the data using homogeneous groups of rats with progression or reversal of liver fibrosis, we identified serum proteins that reflect the activity of hepatic fibrogenesis or fibrolysis, as determined from the paired large-size and thus representative liver samples. This serves as basis for establishing and validating further ELISAs for the most promising of the identified proteins in rat and human serum.

In the following we describe our model of biliary liver fibrosis progression which reverses spontaneously after bile flow is restored.

Example 1

Selection of Time Points of Maximal Fibrogenesis and Fibrolysis in Rat Models of Portal and Panlobular Cirrhosis and their Reversal Induction and Reversion of Biliary Fibrosis Advanced biliary fibrosis/cirrhosis was induced in 36 adult rats by bile duct ligation (BDL) for 4 weeks. At week 5 biliodigestive (Roux-en-Y, RY) anastomosis was performed to drain the congested biliary system. RY anastomosis led to resolution of fibrosis which was monitored for up to 12 weeks. Total and relative liver collagen was quantified as hydroxyproline (HYP) and hepatic transcript levels of genes that are central to fibrogenesis and fibrolysis were quantified by real-time PCR using the TAQMAN™ technique. Gelatinase and collagenase activities were determined from liver homogenates. Connective tissue staining showed advanced biliary fibrosis/incipient cirrhosis 4 weeks after BDL. 4 weeks after RY-anastomosis a marked decrease in periportal fibrosis and fragmentation of the thickened septa were observed. Septa had disappeared 12 weeks after RY-anastomosis, with only slightly enlarged portal tracts remaining (FIG. 1).

Since the liver volume increased 2.6-fold at peak fibrosis (4 weeks after BDL) and normalized at week 12 of recovery, connective tissue staining only allowed assessment of architectural changes rather than of quantitative aspects of fibrolysis. Therefore, relative (per g of liver) and total (per whole liver) collagen content was quantified via hepatic hydroxyproline (HYP) determination. At peak fibrosis total hepatic collagen content had increased 6-fold compared to sham-operated animals. Following RY-anastomosis total hepatic HYP decreased steadily, from 30 mg at peak fibrosis to 9.4 mg per liver at 12 weeks (compared to 5.1 mg for the sham-operated group) (FIG. 2A). Relative hepatic HYP demonstrated a pattern more compatible with connective tissue staining, with a 1.5-fold reduction 2 and 4 weeks after RY-anastomosis (FIG. 2B).

In order to monitor fibrolysis, it is important to determine the enzymatic matrix-degrading activities. Therefore, we quantified interstitial collagenase and gelatinase activities in liver homogenates using biotinylated substrates. Interstitial collagenase activity was elevated at peak of fibrosis (indicating enhanced general ECM turnover) and increased again markedly (6-fold) at week 4 of resolution, coinciding with the most dramatic histological remodeling, i.e., dissolution of septa and prominent infiltration of fibrolytic, MMP-expressing macrophages into the liver tissue (FIGS. 1 and 3A).

Total gelatinase activity was >1.5-fold upregulated at the peak of fibrosis and at 4 weeks of recovery, remaining at baseline at the other time points (FIG. 3B). Interstitial collagenase activity was up-regulated 2-fold at peak fibrosis and reached a 5-fold increase at week 4 of reversal.

Example 2

Quantitative Proteomic Analysis with Isobaric Protein Tags to Identify Serum Markers of Hepatic Fibrogenesis and Fibrolysis

2.1. Optimization and Evaluation of Surface-Enhanced Laser Desorption/Ionization Time-of-Flight Mass Spectrometry (SELDI-TOF MS) with Reversed-Phase Protein Arrays for Protein Profiling SELDI-TOF MS with protein arrays has facilitated the discovery of disease-specific protein profiles in serum[38]. Reliable protein profiles need to be generated from many samples, yielding accurate mass peak heights, and the experimental variation of the profiles must be known. We adapted the entire processing of protein arrays to a robotics system, thus improving the intra-assay coefficients of variation (CVs) from 45.1% to 27.8% ($p<0.001$). In addition, we assessed 16 technical replicates, and demonstrated that analysis of 2-4 replicates significantly increases the reliability of the protein profiles. We discovered that the inter-assay CV is strongly dependent on the drying time before application of the matrix molecule, leading us to devise a standardized drying process. Our optimized SELDI procedure generates reliable and long-term reproducible protein profiles with CVs ranging from 25.7% to 32.6%, depending on the signal-to-noise ratio threshold used.

2.2. Validation of the Methodology for Serum Proteomics and Detection of Biomarkers in Hepatocellular Carcinoma (HCC)

We evaluated the sensitivity and specificity of SELDI-TOF MS and compared against alphafetoprotein (AFP), *lens culinaris*-agglutinin reactive AFP (AFP-L3) and prothrombin induced by vitamin K absence-II (PIVKA-II). 41 patients with HCC and 51 patients with hepatitis C cirrhosis were enrolled. Serum was analyzed using 3 Ciphergen protein array types. An 11 peak algorithm for HCC detection was identified. Using the AFP cutoff of 20 ng/ml, sensitivity was 73% and specificity 71%. Using the PIVKA-II cutoff of 125 mAU, sensitivity was 84% and specificity 69%. Overall sensitivity and specificity of SELDI-TOF MS for HCC were 79% and 86%, resp. In multivariate analysis, the 11-peak SELDI profile was predictive of HCC independently of AFP, PIVKA and AFP-L3. Among 8 patients with the largest tumor size <2 cm, SELDI-TOF MS correctly identified 7 while AFP, AFP-L3, and PIVKAII identified only 3, 1, and 1, resp. One of the 11 peaks identified was Cystatin.

2.3. ITRAQ® Quantitative Serum Proteomics for Identification of Liver Fibrogenesis/Fibrolysis Markers We applied ITRAQ® and MS for identification of liver fibrogenesis/fibrolysis markers, to analyze sera from four experimental groups derived from biliary fibrosis and its regression. Serum from 6-8 rats for each of the 4 selected experimental time points were pooled. The pooled rat serum samples of 150 µl each were depleted of the top 12 rat serum proteins (albumin, IgG, IgM, fibrinogen, transferrin, haptoglobin, antitrypsin) using the BECKMAN COULTER® PROTEOMELAB® IgY-R7 LC10 High Capacity Columns which have been optimized for rodents and enable the processing of up to 200 µl rat serum. Expected yield was 3-5 mg protein. This depletion step is critical to enrich for low abundant proteins, since the top 7 proteins comprise up to >95% of all serum proteins and the dynamic range of proteins in serum is more than ten logs. The Beckman column was used for removal of abundant proteins with great success. This column is a HPLC column, limiting the processing to one sample per run. Alternatively, the BECKMAN COULTER® IgY-R18 spin columns were used. The advantage with these columns is that all samples can be processed in parallel. The disadvantage is that only 15 µl serum can be processed at once, yielding about 200-400 µg of protein.

Depleted serum aliquots from 2 batches of 3-4 rats per experimental group were pooled and the eight pools (70 µl each) were incubated with Pall Ceramic Q Beads rocking at 4° C. for 90 minutes. The beads were then centrifuged. Proteins were selectively eluted from the beads using buffers of decreasing pH (8.1, 7.4, 6.8, 5.0, 3.0) and then with a 50% acetonitrile/0.1% trifluoroacetic acid gradient. Analysis by MALDI MS showed that the fractions of pH 8.1 and 7.4 were mostly free of albumin and were therefore used for further analysis. 100 µg of proteins from this fractionation for each experimental condition were digested with trypsin overnight and then labeled with a different ITRAQ® isobaric tag (ABI) of either 113, 114, 115, 116, 117, 118, 119 or 121 D molecular weight for each sample. Serum from normal rats was labeled with Tag 113, 117, from rats with 4 weeks BDL (max fibrogenesis) with Tag 114, 118, from rats 2 weeks after RY-anastomosis with Tag 115, 119, and from rats 4 weeks after RY-anastomosis with Tag 116, 121 (4 groups, n=2). After labeling the eight tagged rat serum pools were combined and fractionated on the DIONEX™ ULTIMATE™ NanoLC system on one dimension (Reversed Phase)[39]. Fractions were directly collected and spotted by the PROBOT™ robot onto the MALDI target plates together with the matrix for ionization. All fractions were then analyzed on the ABI 4700 MALDI-TOF/TOF mass spectrometer by tandem MS. The data were analyzed by the GPS EXPLORER™ software and the MASCOT® protein database. Each of the peptides also yielded quantitative values for each of the eight tags representing the eight serum samples and ratios of the eight tags to each other.

An example of a MS/MS fragmentation mass spectrum and the relative ratio of a four ITRAQ® tag system for each of those peptides are shown in FIG. 4. For example, a strong upregulation of kininogen 1 in the serum from groups representing early fibrolysis in bile duct ligated rats 2 weeks after RY-anastomosis was observed.

A list of 25 identified proteins by comparative ITRAQ® proteomics of serum pools (n=3-4) from rats with liver fibrosis progression and reversal are shown in Tables 1 and 2.

TABLE 1

| Name | BDL fibrogenesis 114:113 | fibrolysis 2 weeks 115:113 | fibrolysis 4 weeks 116:113 | control 1/ control 2 117:113 | BDL fibrogenesis 118:113 | fibrolysis 2 weeks 119:113 | fibrolysis 4 weeks 121:113 | Fibrolysis (○) | Fibrogenesis (X) |
|---|---|---|---|---|---|---|---|---|---|
| Kininogen-1 | 2.8840 | 5.8076 | 5.4450 | 0.8241 | 1.4060 | 4.6559 | 6.6069 | ○ | |
| Nesprin-1 | 1.9231 | 3.7670 | 4.0926 | 0.9550 | 2.9923 | 3.5645 | 3.9084 | ○ | |
| Vitronectin | 0.0955 | 0.3733 | 0.5916 | 0.7798 | 0.1660 | 0.7178 | 0.6982 | ○ | |
| Niemann-Pick C1-like protein 1 | 1.2942 | 2.9923 | 1.2706 | 0.8551 | 1.4997 | 2.8314 | 2.7797 | ○ | |
| Protocadherin Fat 4 | 0.4742 | 1.6144 | 2.2909 | 1.0280 | 0.9638 | 1.9055 | 2.2909 | ○ | |

TABLE 1-continued

| Name | BDL fibrogenesis 114:113 | fibrolysis 2 weeks 115:113 | fibrolysis 4 weeks 116:113 | control 1/ control 2 117:113 | BDL fibrogenesis 118:113 | fibrolysis 2 weeks 119:113 | fibrolysis 4 weeks 121:113 | Fibrolysis (○) | Fibrogenesis (X) |
|---|---|---|---|---|---|---|---|---|---|
| Probable E3 ubiquitin-protein ligase HERC2 | 2.1281 | 3.2211 | 1.1588 | 0.6668 | 1.8707 | 3.1623 | 4.2462 | ○ | |
| Extracellular matrix protein FRAS1 | 0.4446 | 0.9638 | 0.4699 | 1.1376 | 0.3404 | 1.1169 | 1.0000 | ○ | |
| E3 ubiquitin-protein ligase UBR3 | 4.4463 | 3.4995 | 4.0179 | 1.7378 | 1.2134 | 3.7325 | 5.4954 | ○ | |
| WD repeat-containing protein 90 | 20.7014 | 0.3499 | 2.4660 | 1.4723 | 17.8649 | 1.3552 | 1.6144 | | X |
| Ephrin type-B receptor 3 | 79.4328 | 0.9908 | 0.9908 | 0.9908 | 78.7046 | 0.9908 | 0.9908 | | X |
| Probable E3 ubiquitin-protein ligase MYCBP2 | 1.1803 | 2.4434 | 2.3988 | 0.6918 | 1.3677 | 2.4210 | 2.3768 | ○ | |
| Transient receptor potential cation channel subfamily M member 4 | 11.2720 | 1.0000 | 0.5105 | 0.7244 | 8.1658 | 0.1057 | 0.6486 | | X |
| Protein FAM71B | 1.6144 | 3.6644 | 3.7670 | 0.5445 | 0.9120 | 2.8314 | 4.2073 | ○ | |
| WD repeat-containing protein 85 | 1.8030 | 2.7542 | 3.2509 | 1.3804 | 1.0186 | 2.6792 | 3.0200 | ○ | |
| E3 ubiquitin-protein ligase UBR2 | 2.4434 | 4.4463 | 2.6546 | 0.6427 | 0.9462 | 3.1046 | 2.5823 | ○ | |
| Transmembrane protein 206 | 3.1333 | 7.7983 | 5.6494 | 1.2023 | 1.9588 | 4.7863 | 5.8076 | ○ | |
| Mucin-6 | 2.0137 | 4.3652 | 1.0965 | 1.1912 | 1.9231 | 4.4055 | 5.5463 | ○ | |
| Myotubularin-related protein 9 | 5.1051 | 1.0568 | 1.0864 | 0.8166 | 4.4463 | 0.6546 | 1.0186 | | X |
| Nck-associated protein 1 | 4.9204 | 0.8954 | 1.3062 | 0.8954 | 4.2855 | 0.6081 | 0.9376 | | X |
| Vesicular glutamate transporter 2 | 4.3251 | 0.9908 | 1.1482 | 0.7943 | 3.1333 | 0.5248 | 0.8017 | | X |
| Arf-GAP with GTPase, ANK repeat and PH domain-containing protein 3 | 1.9055 | 3.1623 | 2.9648 | 1.0965 | 1.8707 | 3.3419 | 4.0551 | ○ | |
| Slit homolog 2 protein | 6.2517 | 1.2474 | 2.2699 | 1.6444 | 5.0582 | 1.7061 | 1.4997 | | X |
| Beta-1,3-galactosyl-O-glycosyl-glycoprotein beta-1,6-N-acetylglucosaminyltransferase 7 | 0.1419 | 0.3802 | 0.7178 | 0.9376 | 0.1500 | 0.6982 | 0.5105 | ○ | |
| Fibronectin type III domain containing protein 3C1 | 4.1687 | 1.2246 | 0.9638 | 1.1169 | 3.5645 | 1.2023 | 1.3428 | | X |
| Homeobox even-skipped homolog protein 1 | 7.3114 | 0.7656 | 1.6904 | 0.9550 | 6.6681 | 0.8954 | 1.1695 | | X |

BDL = bile duct ligation

TABLE 2

| iTRAQ label | sample name | State of fibrosis | Time point |
|---|---|---|---|
| 113 | 1A | normal control | 0 |
| 114 | 2A | fibrogenesis | BDL 4 weeks |
| 115 | 3A | reversal 2 weeks | RY 2 weeks |
| 116 | 4A | reversal | RY 4 weeks |
| 117 | 1B | normal control | 0 |
| 118 | 2B | fibrogenesis | BDL 4 weeks |
| 119 | 3B | reversal | RY 2 weeks |
| 121 | 4B | reversal | RY 4 weeks |

Example 3

Validation of ITRAQ® Methodology by Repeat Analyses of Different Serum Pools and by Quantifying Select Markers in Serum Pools and Individual Sera In order to evaluate whether the measurements are accurate and reproducible, experiments were repeated with different pools, and experimental variations of the previous conditions were applied. E.g., 30 µl of serum were depleted of the top 7 most abundant proteins (Albumin, IgG, α1-antitrypsin, IgM, transferrin, haptoglobin and fibrinogen) for each pool. 100 µg of protein from each thus depleted sample were then purified by acetone precipitation, digested with trypsin and labeled with the ITRAQ® reagents: normal rat serum was labeled with Tag 114, 4 weeks BDL with Tag 115, 2 weeks after RY-anastomosis with Tag 116, and 4 weeks after RY-anastomosis with Tag 117 (Groups 1, 2, 3 and 4). After labeling the four tagged rat serum pools were combined and fractionated using a strong cation exchange chromatography (POROS™ HS20) on an Agilent 1100 HPLC. The labeled peptides were collected as 12 fractions. Each fraction was then injected in a DIONEX™ ULTIMATE™ NanoLC system for further fractionation by Reversed Phase[39]. Fractions were directly collected and spotted by the PROBOT™ robot onto the MALDI target plates together with the matrix for ionization. All fractions were then analyzed on the ABI 4700 MALDI-TOF/TOF mass spectrometer by tandem MS.

As an example kininogen 1 was again identified as consistently upregulated in every condition of fibrolysis as compared to normal (FIG. 5).

These results were further validated by an ELISA for rat kininogen 1 (Life Diagnostics) on the pools used for ITRAQ® experiments as well as on the individual samples composing pools A. Serum samples were diluted 1:10,000 and ran in duplicate. In order to be able to compare the ITRAQ® results with the ELISA data, the relative ratios of all kininogen 1 peptides retrieved with ITRAQ® were averaged per condition and normalized to condition 1 (normal serum). The upregulation identified by the ITRAQ® finding was confirmed by the ELISA results (FIG. 5). Thus the serum levels of kininogen 1 were mildly elevated at peak fibrosis and increased markedly at weeks 2>4 of fibrosis reversal (maximal fibrolysis) after biliary drainage, as determined with both the ITRAQ® and ELISA methodologies. Interestingly, corresponding hepatic transcript levels of urokinase plasminogen activator receptor, furin, and MMP-9, all key molecules of fibrolysis, were most highly increased at week 2 and to a lesser degree at week 4 of reversal.

REFERENCES

1. Schuppan D, Afdhal N H. Lancet Seminars: Liver cirrhosis. Lancet 2008; 371:838-51.
2. Castera L. Noninvasive methods to assess liver disease in patients with hepatitis B or C. Gastroenterology 2012; 142:1293-1302.

3. Friedman S L. Evolving challenges in hepatic fibrosis. Nat Rev Gastroenterol Hepatol 2010; 7:425-36.
4. Popov Y, Schuppan D. Targeting liver fibrosis: strategies for development and validation of antifibrotic therapies. Hepatology 2009; 50:1294-1306.
5. Schuppan D, Pinzani M. Anti-fibrotic therapy: lost in translation? J Hepatol 2012; 56 Suppl 1:S66-74.
6. Fernandez M, Semela D, Bruix J, Colle I, Pinzani M, Bosch J. Angiogenesis in liver disease. J Hepatol 2009; 50:604-620.
7. Bravo A A, Sheth S G, Chopra S. Liver biopsy. N Engl J Med 2001; 344:495-500.
8. Regev A, Berho M, Jeffers L J, et al. Sampling error and intraobserver variation in liver biopsy in patients with chronic HCV infection. Am J Gastroenterol 2002; 97:2614-2618.
9. Bedossa P, Dargere D, Paradis V. Sampling variability of liver fibrosis in chronic hepatitis C. Hepatology 2003; 38:1449-1457.
10. Ratziu V, Charlotte F, Heurtier A, Gombert S, Giral P, Bruckert E, Grimaldi A, et al. Sampling variability of liver biopsy in nonalcoholic fatty liver disease. Gastroenterology 2005; 128:1898-1906.
11. Olsson R, Hagerstrand I, Broome U, Danielsson A, Jarnerot G, Loof L, Prytz H, et al. Sampling variability of percutaneous liver biopsy in primary sclerosing cholangitis. J Clin Pathol 1995; 48:933-935.
12. Cisneros L, Londono M C, Blasco C, et al. Hepatic stellate cell activation in liver transplant patients with hepatitis C recurrence and in non-transplanted patients with chronic hepatitis C. Liver Transpl 2007; 13:1017-1027.
13. Gabrielli G B, Casaril M, Stanzial A M, et al. Liver stellate cells and aminoterminal peptide of type III procollagen in chronic hepatitis C treated with interferon. Hepatogastroenterology 2003; 50:2017-2021.
14. Pinzani M, Vizzutti F, Arena U, Marra F. Technology Insight: noninvasive assessment of liver fibrosis by biochemical scores and elastography. Nat Clin Pract Gastroenterol Hepatol 2008; 5:95-106.
15. Adams L A. Biomarkers of liver fibrosis. J Gastroenterol Hepatol 2011; 26:802-9.
16. Guha I N, Myers R P, Patel K, Talwalkar J A. Biomarkers of liver fibrosis: what lies beneath the receiver operating characteristic curve? Hepatology 2011; 5:1454-62.
17. Martinez S M, Crespo G, Navasa M, Forns X. Noninvasive assessment of liver fibrosis. Hepatology 2011; 53:325-35.
18. Poynard T, Halfon P, Castera L, et al. Standardization of ROC curve areas for diagnostic evaluation of liver fibrosis markers based on prevalences of fibrosis stages. Clin Chem 2007; 53:1615-22.
19. Mehta S H, Lau B, Afdhal N H, Thomas D L. Exceeding the limits of liver histology markers. J Hepatol 2009; 50:36-41.
20. Talwalkar J A, Yin M, Fidler J L, et al. Magnetic resonance imaging of hepatic fibrosis: emerging clinical applications. Hepatology 2008; 47:332-42.
21. Faria S C, Ganesan K, Mwangi I, et al. MR imaging of liver fibrosis: current state of the art. Radiographics 2009; 29:1615-35.
22. Ferraioli G, Tinelli C, Bello B D, et al. Accuracy of real-time shear wave elastography for assessing liver fibrosis in chronic hepatitis C: A pilot study. Hepatology 2012 Jul. 5. doi: 10.1002.
23. Huwart L, Sempoux C, Vicaut E, et al. Magnetic resonance elastography for the noninvasive staging of liver fibrosis. Gastroenterology 2008; 135:32-40.
24. Parkes J, Guha I N, Roderick P, Rosenberg W. Performance of serum marker panels for liver fibrosis in chronic hepatitis C. J Hepatol 2006; 44:462-74.
25. Manning D S, Afdhal N H. Diagnosis and quantitation of fibrosis. Gastroenterology 2008; 134:1670-1681.
26. Thein H H, Yi Q, Dore G J, Krahn M D. Estimation of stage-specific fibrosis progression rates in chronic hepatitis C virus infection: a meta-analysis and meta-regression. Hepatology 2008; 48:418-431.
27. Poynard T, Zoulim F, Ratziu V, Degos F, Imbert-Bismut F, Deny P, Landais P, et al. Longitudinal assessment of histology surrogate markers (FibroTest-ActiTest) during lamivudine therapy in patients with chronic hepatitis B infection. Am J Gastroenterol 2005; 100:1970-1980.
28. Naveau S, Gaude G, Asnacios A, Agostini H, Abella A, Barri-Ova N, Dauvois B, et al. Diagnostic and prognostic values of noninvasive biomarkers of fibrosis in patients with alcoholic liver disease. Hepatology 2009; 49:97-105.
29. Mayo M J, Parkes J, Adams-Huet B, Combes B, Mills A S, Markin R S, Rubin R, et al. Prediction of clinical outcomes in primary biliary cirrhosis by serum enhanced liver fibrosis assay. Hepatology 2008; 48:1549-1557.
30. Parkes J, Roderick P, Harris S, et al. Enhanced liver fibrosis test can predict clinical outcomes in patients with chronic liver disease. Gut 2010; 59:1245-51.
31. Fontana R J, Dienstag J L, Bonkovsky H L, et al. Serum fibrosis markers are associated with liver disease progression in non-responder patients with chronic hepatitis C. Gut 2010; 59:1401-9.
32. Nagula S, Jain D, Groszmann R J, Garcia-Tsao G. Histological-hemodynamic correlation in cirrhosis—a histological classification of the severity of cirrhosis. J Hepatol 2006; 44:111-117.
33. Ripoll C, Groszmann R, Garcia-Tsao G, Grace N, Burroughs A, Planas R, Escorsell A, et al. Hepatic venous pressure gradient predicts clinical decompensation in patients with compensated cirrhosis. Gastroenterology 2007; 133:481-488.
34. Kim M Y, Suk K T, Baik S K, et al. Hepatic vein arrival time as assessed by contrast-enhanced ultrasonography is useful for the assessment of portal hypertension in compensated cirrhosis. Hepatology 2012 Apr. 2. doi: 10.1002/hep.25752.
35. Nista E C, Fini L, Armuzzi A, et al. 13C-breath tests in the study of microsomal liver function. Eur Rev Med Pharmacol Sci 2004; 8:33-46.
36. Kornek M, Schuppan D. Microparticles: Modulators and biomarkers of liver disease. J Hepatol 2012 Aug. 6.
37. Wang X W, Heegaard N H, Orum H. MicroRNAs in liver disease. Gastroenterology 2012; 142:1431-43.
38. Aivado M, Spentzos D, Alterovitz G, Otu H H, Grail F, Giagounidis A A, Wells M, Cho J Y, Germing U, Czibere A, Prall W C, Porter C, Ramoni M F, Libermann T A. Optimization and evaluation of surface-enhanced laser desorption/ionization time-of-flight mass spectrometry (SELDI-TOF MS) with reversed-phase protein arrays for protein profiling. Clin Chem Lab Med 2005; 43(2):133-40.
39. Chen H S, Rejtar T, Andreev V, Moskovets E, Karger B L. High-speed, high-resolution monolithic capillary LC-MALDI MS using an off-line continuous deposition interface for proteomic analysis. Anal Chem 2005 Apr. 15; 77(8):2323-31.

The invention claimed is:

1. A method comprising the steps of:
   a) measuring in a biological sample from a human or animal subject suspected of having a liver disease a level of two or more protein biomarkers selected from the group consisting of: Transmembrane protein 206, Kininogen-1, ubiquitin protein ligase E3 component N-recognin 3 (UBR3), Mucin-6, Nesprin-1, Protein Family with Sequence Similarity 71 Member B (FAM71B), and peptide fragments thereof, and
   b) administering a treatment for said liver disease to said subject having an increased level of at least two of said biomarkers, as compared to a control.

2. The method according to claim 1, wherein said biomarkers are proteins selected from the group consisting of: Transmembrane protein 206, Kininogen-1, UBR3, Mucin-6, Nesprin-1, and Protein FAM71B.

3. The method of claim 1, wherein said biological sample is a body fluid.

4. The method of claim 3, wherein the body fluid is blood, serum, plasma, or urine.

5. A method of measuring a level of two or more protein biomarkers, said method comprising:
   a) contacting a biological sample from a subject suspected of having a liver disease with detecting agents that bind two or more protein biomarkers selected from the group consisting of: Transmembrane protein 206, Kininogen-1, UBR3, Mucin-6, Nesprin-1, Protein FAM71B, and peptide fragments thereof, and
   b) measuring the level of said biomarkers in the sample that are bound by the detecting agents.

6. The method of claim 5, wherein said detecting agents are capable of binding to a solid support.

7. The method of claim 5, wherein said detecting agents contain a detectable label or are conjugated to a detectable label.

8. The method of claim 5, wherein said detecting agents are antibodies, antibody fragments, or derivatives thereof.

9. The method of claim 5, wherein said two or more biomarkers are measured by an enzyme linked immunosorbent assay (ELISA).

* * * * *

UNITED STATES PATENT AND TRADEMARK OFFICE
CERTIFICATE OF CORRECTION

Page 1 of 1

PATENT NO. : 10,884,001 B2
APPLICATION NO. : 15/110288
DATED : January 5, 2021
INVENTOR(S) : Detlef Schuppan et al.

It is certified that error appears in the above-identified patent and that said Letters Patent is hereby corrected as shown below:

In the Specification

Column 1, Line 2, insert:
--STATEMENT OF FEDERALLY SPONSORED RESEARCH
This invention was made with government support under Grant No. DK076873 awarded by the National Institutes of Health. The government has certain rights in this invention.--

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Asn Ile Pro Val Asp Ser Pro Glu Leu Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Ala Thr Ser Gln Val Val Ala Gly Thr Lys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Ile Asp Thr Val Lys Lys
1               5